(12) United States Patent
Grote et al.

(10) Patent No.: US 8,563,724 B2
(45) Date of Patent: Oct. 22, 2013

(54) (+)-6-HYDROXY-MORPHINAN OR (+)-6-AMINO-MORPHINAN DERIVATIVES

(75) Inventors: Christopher W. Grote, Webster Groves, MO (US); Gary L. Cantrell, Troy, IL (US); Peter X. Wang, Clarkson Valley, MO (US); Bobby N. Trawick, Florissant, MO (US); David W. Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 583 days.

(21) Appl. No.: 12/710,390

(22) Filed: Feb. 23, 2010

(65) Prior Publication Data

US 2010/0216995 A1    Aug. 26, 2010

Related U.S. Application Data

(60) Provisional application No. 61/154,449, filed on Feb. 23, 2009.

(51) Int. Cl.
*C07D 489/00* (2006.01)

(52) U.S. Cl.
USPC .......................................................... 546/44

(58) Field of Classification Search
USPC .......................................................... 546/44
See application file for complete search history.

(56) References Cited

U.S. PATENT DOCUMENTS

| 5,739,145 | A  | 4/1998  | Nagase et al. |
| 6,174,891 | B1 | 1/2001  | Nagase et al. |
| 6,277,859 | B1 | 8/2001  | Nagase et al. |
| 2004/0077863 | A1 | 4/2004 | Scammells et al. |
| 2004/0204434 | A1 | 10/2004 | Shafer et al. |
| 2005/0182258 | A1 | 8/2005 | Schmidhammer et al. |
| 2006/0258696 | A1 | 11/2006 | Moss et al. |
| 2007/0265293 | A1 | 11/2007 | Boyd et al. |
| 2008/0161570 | A1 | 7/2008 | Perez et al. |
| 2008/0176884 | A1 | 7/2008 | Perez et al. |
| 2008/0207669 | A1 | 8/2008 | Perez et al. |
| 2008/0214817 | A1 | 9/2008 | Dlubala |
| 2008/0234306 | A1 | 9/2008 | Perez et al. |
| 2008/0274119 | A1 | 11/2008 | Moss et al. |
| 2009/0062544 | A1 | 3/2009 | Wakita et al. |

FOREIGN PATENT DOCUMENTS

| CH | 683 005 A5 | 12/1993 |
| DE | 1119284 | 12/1961 |
| EP | 0 418 591 | 3/1991 |
| JP | 2001-302668 | 10/2001 |
| WO | WO 01/14382 | 3/2001 |
| WO | WO 01/74819 | 4/2001 |
| WO | WO 2004/043964 | 5/2004 |
| WO | WO 2005/0028483 | 3/2005 |
| WO | WO 2006/096626 | 9/2006 |
| WO | WO 2006/127899 | 11/2006 |

OTHER PUBLICATIONS

Dolle, et al. (Document No. 144:397383, CAPLUS) 2006.*
Tanabe (Document No. 144:445378, CAPLUS) 2006.*
Kelentey et al., "Preparation and pharmacological properties of n-oxides of opium alkaloids", Kiserletes orvostudomany, 1958, 10(1), pp. 70-77.
Kelentey et al., "Preparation and pharmacological studies of n-oxides of opium alkaloids", Arzneimittel-Forschung, 1957, 7, pp. 594-597.
Takagi et al., "Antitussive Activity of the N-Oxides of Opium Alkaloids", Journal of the Pharmaceutical Society of Japan, 77 (11), 1957 p. 1358.
Takagi et al., "Studies on Antitussives. II. Opium Alkaloids and their N-Oxides", Journal of the Pharmaceutical Society of Japan, 80(10), 1960, pp. 1501-1506.
Heumans et al., "Some aspects of the metabolism of morphine-$N$-oxide", J. Pharm. Pharmac., 1971, 23, pp. 831-836.
Bao et al., "Morphinane Alkaloids with Cell Protective Effects from *Sinomenium acutum*", J. Nat. Prod., 2005, 68, pp. 1128-1130.
Makareviche et al., "Quaternary Salts of Alkaloids", Chemistry of Natural Compounds, 2006, 42(4), pp. 473-476.

* cited by examiner

*Primary Examiner* — Shawquia Young

(57) ABSTRACT

The present invention provides (+)-morphinanium compounds comprising substituted 6-hydroxy or 6-amine groups. The invention also provides methods for inhibiting microglial activation by administering the compounds of the invention.

10 Claims, No Drawings

(+)-6-HYDROXY-MORPHINAN OR (+)-6-AMINO-MORPHINAN DERIVATIVES

CROSS REFERENCE TO RELATED APPLICATIONS

This application claims priority from U.S. Provisional Application No. 61/154,449 filed on Feb. 23, 2009, which is hereby incorporated by reference in its entirety.

FIELD OF THE INVENTION

The present invention generally relates to substituted (+)-6-hydroxy-morphinans or substituted (+)-6-amine-morphinans and methods of using substituted (+)-6-hydroxy-morphinans or substituted (+)-6-amine-morphinans to inhibit microglial activation in the central nervous system.

BACKGROUND OF THE INVENTION

Microglia serve as the first and main form of active immune defense in the central nervous system. These cells are believed to be functionally equivalent to monocytes or tissue macrophages of the somatic immune system. It has long been recognized that microglia migrate to, differentiate and proliferate at sites of brain injury and inflammation. Thus, activation of microglia appears to play a major role in numerous neuroinflammatory diseases or disorders. Furthermore, microglial activation is modulated by opiates and has been implicated in opiate dependence and the development of tolerance. The mu opiate receptor antagonists, (−)-naloxone and (−)-naltrexone, have been shown to inhibit the proinflammatory pathway involved in microglial activation. Inhibition of microglial activation is non-stereoselective, however, in that the (+) mirror enantiomers of naloxone and naltrexone have been shown to retain microglial inhibitory activity. Thus, (+)-morphinan compounds may be useful for treating inflammatory diseases, as antitussive agents, or for reducing the potential of opiate abuse and dependence. Substitution at position 6 of the morphinan ring may provide compounds that function as prodrugs with increased activity relative to the unfunctionalized precursors. There is a need, therefore, for mirror image enantiomorph (+)-morphinan compounds with substituted hydroxy or amino groups at position 6.

SUMMARY OF THE INVENTION

The present invention provides substituted (+)-6-hydroxy-morphinans or substituted (+)-6-amine-morphinans, as well as methods of using the substituted (+)-6-hydroxy- or (+)-6-amine-morphinans to inhibit microglial activation.

One aspect of the present invention encompasses a compound comprising Formula (II) or a pharmaceutically acceptable salt thereof:

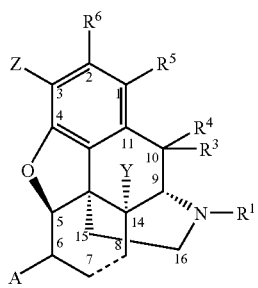

(II)

wherein:
A is selected from the group consisting of {—}$OR^8$ and {—}$NR^8R^9$;
$R^1$ is selected from the group consisting of hydrocarbyl and substituted hydrocarbyl;
$R^3$, $R^4$, $R^8$, and $R^9$ are independently selected from the group consisting of hydrogen, hydrocarbyl, and substituted hydrocarbyl;
$R^5$ and $R^6$ are independently selected from the group consisting of hydrogen, hydrocarbyl, substituted hydrocarbyl, halogen, {—}OH, {—}$NH_2$, and {—}$OR^7$;
$R^7$ is selected from the group consisting of hydrocarbyl and substituted hydrocarbyl;
Y is selected from the group consisting of hydrogen, hydroxy, protected hydroxy, alkoxy, and acyloxy;
Z is selected from the group consisting of hydroxy, protected hydroxy, alkoxy, and acyloxy; and
the dashed line between the carbon atoms at positions 7 and 8 represents a single bond or a double bond.

Another aspect of the present invention provides a compound comprising Formula (I) or a pharmaceutically acceptable salt thereof:

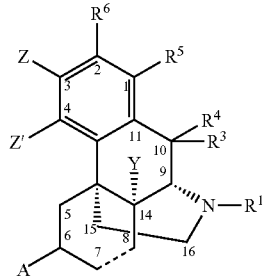

(I)

wherein:
A is selected from the group consisting of {—}$OR^8$ and {—}$NR^8R^9$;
$R^1$ is selected from the group consisting of hydrocarbyl and substituted hydrocarbyl;
$R^3$, $R^4$, $R^8$, and $R^9$ are independently selected from the group consisting of hydrogen, hydrocarbyl, and substituted hydrocarbyl;
$R^5$ and $R^6$ are independently selected from the group consisting of hydrogen, hydrocarbyl, substituted hydrocarbyl, halogen, {—}OH, {—}$NH_2$, and {—}$OR^7$;
$R^7$ is selected from the group consisting of hydrocarbyl and substituted hydrocarbyl;
Y is selected from the group consisting of hydrogen, hydroxy, protected hydroxy, alkoxy, and acyloxy;
Z is selected from the group consisting of hydroxy, protected hydroxy, alkoxy, and acyloxy;
Z' is selected from the group consisting of hydrogen, hydroxy, protected hydroxy, alkoxy, and acyloxy; and
the dashed line between the carbon atoms at positions 7 and 8 represents a single bond or a double bond.

Other aspects and iterations of the invention are described in more detail below.

DETAILED DESCRIPTION OF THE INVENTION

The present invention provides substituted (+)-6-hydroxy-morphinans or substituted (+)-6-amino-morphinans. The compounds of the present invention are mirror image enantiomers of naturally occurring opiate alkaloids. The substituted (+)-6-hydroxy- or (+)-6-amino-morphinans preferentially bind to glia (i.e., microglia and astrocytes) of the central nervous system and inhibit their activation.

(I) Substituted (+)-6-Hydroxy- or 6-Amino-Morphinan Compounds (a) Compounds Comprising Formula (II)

One aspect of the present invention encompasses a compound comprising

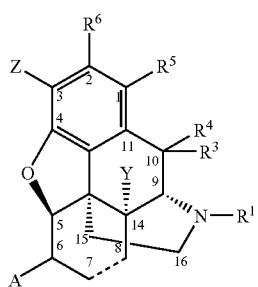

(II)

Formula (II) or a pharmaceutically acceptable salt thereof:
wherein:
A is selected from the group consisting of {—}OR$^8$ and {—}NR$^8$R$^9$;
R$^1$ is selected from the group consisting of hydrocarbyl and substituted hydrocarbyl;
R$^3$, R$^4$, R$^8$, and R$^9$ are independently selected from the group consisting of hydrogen, hydrocarbyl, and substituted hydrocarbyl;
R$^5$ and R$^6$ are independently selected from the group consisting of hydrogen, hydrocarbyl, substituted hydrocarbyl, halogen, {—}OH, {—}NH$_2$, and {—}OR$^7$;
R$^7$ is selected from the group consisting of hydrocarbyl and substituted hydrocarbyl;
Y is selected from the group consisting of hydrogen, hydroxy, protected hydroxy, alkoxy, and acyloxy;
Z is selected from the group consisting of hydroxy, protected hydroxy, alkoxy, and acyloxy; and
the dashed line between the carbon atoms at positions 7 and 8 represents a single bond or a double bond.

In preferred iterations, R$^3$, R$^4$, R$^5$, and R$^6$ are each hydrogen.

In one embodiment of this aspect of the invention, the compound comprises

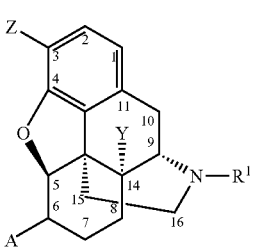

(IIa)

Formula (IIa) or a pharmaceutically acceptable salt thereof:
wherein:
A, R$^1$, R$^8$, and R$^9$, Y and Z are as defined above for compounds comprising Formula (II).

Representative compounds comprising Formula (IIa) or pharmaceutically acceptable salts thereof include (+)-nalbuphine and (+)-nalfurafine.

In another embodiment of this aspect of the invention, the compound comprises

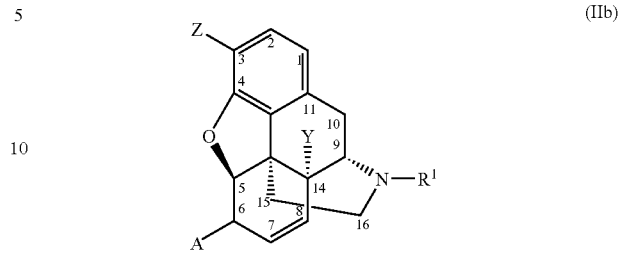

(IIb)

Formula (IIb) or a pharmaceutically acceptable salt thereof:
wherein:
A, R$^1$, R$^8$, and R$^9$, Y and Z are as defined above for compounds comprising Formula (II).

In each of the embodiments for compounds comprising Formula (II), (IIa) or (IIb), provided, however, that when A is {—}OH, {—}O(CO)CH$_3$, {—}NH(CH$_2$)$_2$OH, {—}NH(CO)CH$_3$, or {—}NH$_2$, then R$^1$ is other than methyl.

In each of the for compounds comprising Formula (II), (IIa) or (IIb), provided, however, that when A is {—}OH, {—}NH(CH$_2$)$_2$OH, or {—}NH(CO)CH$_3$, then R$^1$ is other than {—}CH$_2$(CH)CH$_2$.

In each of the embodiments for compounds comprising Formula (II), (IIa) or (IIb), provided, however, that when A is {—}OH, {—}NCH$_3$(CO)CH(CH)(CH)$_4$O, {—}NH(CH$_2$)$_2$OH, {—}NH(CO)CH$_3$, {—}NH$_2$, or {—}NHCH$_3$ then R$^1$ is other than {—}CH$_2$(cyclopropane).

In each of the embodiments for compounds comprising Formula (II), (IIa) or (IIb), provided, however, that when A is {—}OH, then R$^1$ is other than {—}CH$_2$(cyclobutane).

(b) Compounds Comprising Formula (I)

Another aspect of the present invention encompasses a compound comprising Formula (II) or a pharmaceutically acceptable salt thereof:

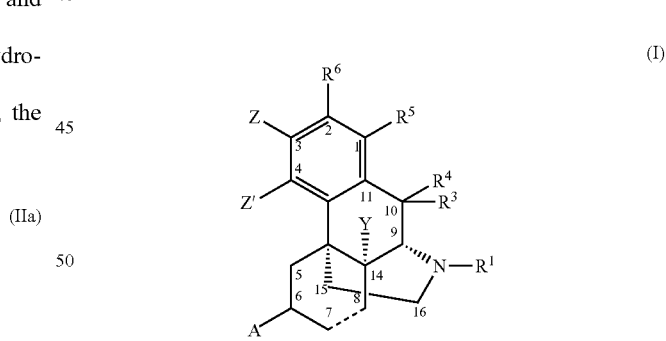

(I)

wherein:
A is selected from the group consisting of {—}OR$^8$ and {—}NR$^8$R$^9$;
R$^1$ is selected from the group consisting of hydrocarbyl and substituted hydrocarbyl;
R$^3$, R$^4$, R$^8$, and R$^9$ are independently selected from the group consisting of hydrogen, hydrocarbyl, and substituted hydrocarbyl;
R$^5$ and R$^6$ are independently selected from the group consisting of hydrogen, hydrocarbyl, substituted hydrocarbyl, halogen, {—}OH, {—}NH$_2$, and {—}OR$^7$;
R$^7$ is selected from the group consisting of hydrocarbyl and substituted hydrocarbyl;

Y is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed line between the carbon atoms at positions 7 and 8 represents a single bond or a double bond.

In preferred iterations, $R^3$, $R^4$, $R^5$, and $R^6$ are hydrogen.

In one embodiment of this aspect of the invention, the compound comprises Formula (Ia) or a pharmaceutically acceptable salt thereof:

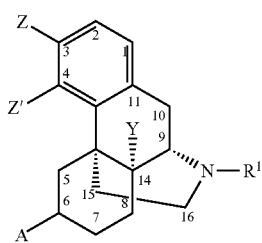

(Ia)

wherein:

A, $R^1$, $R^8$, and $R^9$, Y, Z and Z' are as defined above for compounds comprising Formula (I).

In a further embodiment of this aspect of the invention, the compound comprises Formula (Ib) or a pharmaceutically acceptable salt thereof:

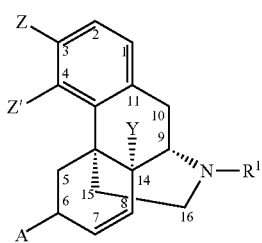

(Ib)

wherein:

A, $R^1$, $R^8$, and $R^9$, Y, Z and Z' are as defined above for compounds comprising Formula (I).

In preferred iterations of the afore-mentioned embodiments, $R^1$ is alkyl, cycloalkyl, cycloalkylmethyl, alkenyl, alkynyl, or aryl. In more preferred iterations, $R^1$ is cyclopropylmethyl, cyclobutylmethyl, allyl, propargyl, or benzyl. Preferably, A is hydroxy, alkoxy, acyloxy, amine, alkyl substituted amine, amido, carbamyl (i.e., {—}OCNH$_2$), carbonate, or urea. In iterations wherein A is alkoxy, the alkyl substituent is preferably lower alkyl. In iterations wherein A is acyloxy (i.e., {—}OC(=O)R), the R substituent is hydrogen, hydrocarbyl, substituted hydrocarbyl, or heterocyclo. In iterations wherein A is an amine (i.e., {—}NR'R"), R' is hydrogen, hydrocarbyl, or substituted hydrocarbyl, and R" is hydrocarbyl, or substituted hydrocarbyl. In iterations wherein A is an alkyl substituted amine, the alkyl is preferably lower alkyl. In iterations wherein A is amido (i.e., {—}NR'(=O)R"), the R substituents generally are independently hydrogen, lower alkyl, substituted lower alkyl, lower alkenyl, or substituted lower alkenyl. In iterations wherein A is carbonate (i.e., {—}OC(=O)R or {—}NR'C(=O)R"), the R groups are independently hydrogen, hydrocarbyl, or substituted hydrocarbyl. In iterations in which A is urea (i.e., {—}NR'C(=O)NHR"), the R groups are independently hydrogen, hydrocarbyl, or substituted hydrocarbyl.

Each of the compounds comprising Formulas (II), (IIa), (IIb), (I), (Ia), (Ib), or a pharmaceutically acceptable salt thereof has a (+) orientation with respect to the rotation of polarized light. More specifically, each chiral center has an R or an S configuration. In particular, the carbon at position 5, if chiral, has an S configuration, the carbon at position 13 has an R configuration, the carbon at position 14 has an R configuration, and the carbon at position 9 has an S configuration. Furthermore, the carbon at position 6 may comprise an S or an R configuration. Stated another way, the substituted ring at position 5, if present, is in the beta position, and the Y group at position 14 is in the alpha position.

Pharmaceutically acceptable salts of compounds comprising Formulas (II), (IIa), (IIb), (I), (Ia), or (Ib) include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, make, citrate, isocitrate, succinate, lactate, gluconate, glucuronate, pyruvate, oxalate, fumarate, propionate, aspartate, glutamate, benzoate, terephthalate, and the like.

(II) Methods for Inhibiting Activation of Microglia

Another aspect of the invention provides methods for inhibiting activation of microglia in a subject. The methods of the invention comprise administering to the subject a compound comprising Formulas (II), (IIa), (IIb), (I), (Ia), (Ib), or a pharmaceutically acceptable salt thereof. The compounds comprising Formulas (II), (IIa), (IIb), (I), (Ia), and (Ib) are detailed above in section (I).

The compound may be administered to the subject in accord with known methods. Typically, the compound will be administered orally, but other routes of administration such as parenteral or topical may also be used. The amount of compound that is administered to the subject can and will vary depending upon the type of compound, the condition being treated, the subject, and the particular mode of administration. Those skilled in the art will appreciate that dosages may be determined with guidance from Goodman & Goldman's The Pharmacological Basis of Therapeutics, Tenth Edition (2001), Appendix II, pp. 475-493, and the Physicians' Desk Reference.

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses "aryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl is the preferred aryl.

The terms "halogen" or "halo" as used herein alone or as part of another group refer to chlorine, bromine, fluorine, and iodine.

The term "heteroatom" refers to atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom, wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Preparation of (+)-Nalfurafine

The following reaction scheme depicts the synthesis of (+)-nalfurafine:

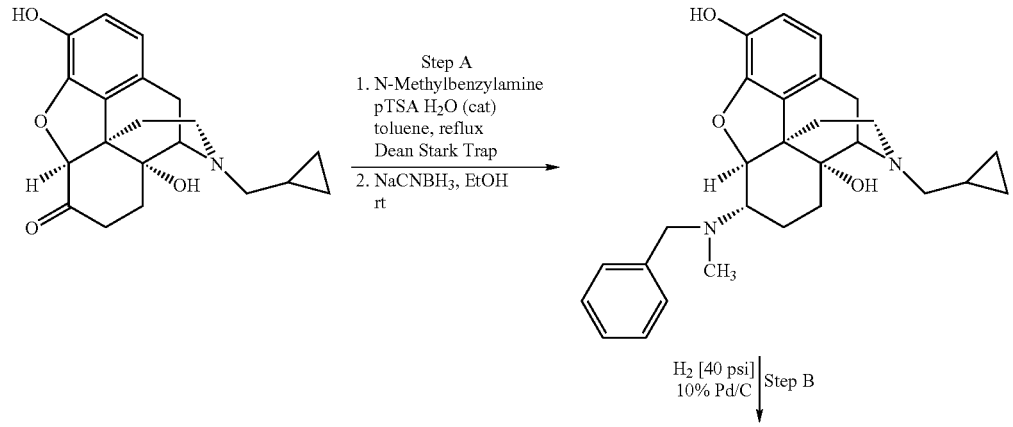

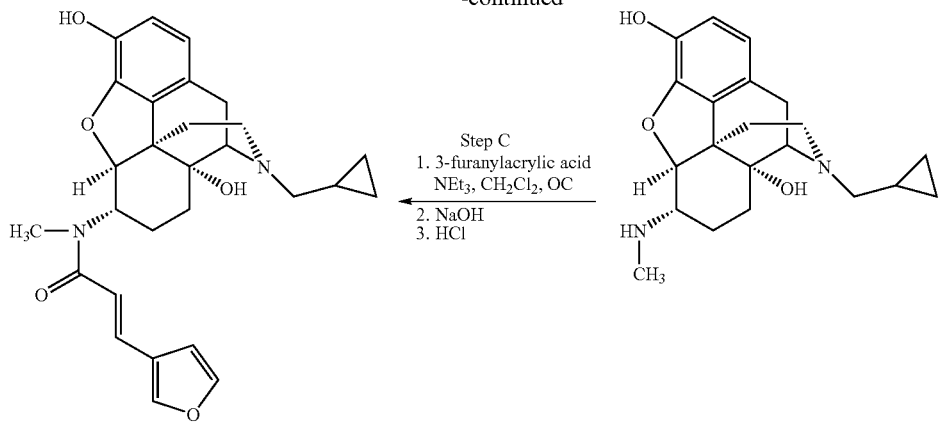

Step A: (+)-Naltrexone (2.0 g, 0.006 moles), N-methylbenzylamine (1.07 g, 0.009 moles), p-toluenesulfonic acid monohydrate (10 mg), and toluene (50 mL) may be introduced into a flask equipped with a Dean Stark Trap. This mixture may be heated to reflux for 12 h over which time water may be removed as an azeotrope. The Dean Stark trap may be exchanged for a short path distillation apparatus. Approximately half the reaction solvent (~25 mL) may be removed through distillation. Upon cooling to room temperature, absolute ethanol (25 mL) may be was introduced followed by NaCNBH$_3$ (390 mg, 0.006 moles). The reaction may be stirred for 6 h at room temperature. Then, distilled water (15 mL) may be added. After stirring for 1 h at room temperature, the mixture may be extracted with ethyl acetate (3×25 mL), the extracts may be combined, dried over anhydrous MgSO$_4$ (~2 g), filtered, and evaporated to dryness. The residue may be chromatographed on SiO$_2$ with 100% EtOAc elution to produce the product (estimated at 1.57 g).

Step B: 6α-N,N-methylbenzyl-(+)-naltrexamine (1.57 g, 0.0035 moles) may be dissolved in glacial acetic acid (20 mL). 10% Pd/C, 50% wet (20 mg) may be added to the Parr bottle containing the reaction mixture. After replacing the atmosphere with hydrogen, the Parr bottle may be pressurized to 40 psi with hydrogen gas. The reaction may be incubated at room temperature for 6 h with shaking (with the hydrogen in the Parr bottle being periodically replaced). After the reaction is deemed complete by HPLC, the contents may be filtered through a celite pad (~1 g of celite), followed by rinsing the pad with glacial acetic acid (5 mL). The filtrate may be cooled to ice-bath temperature, and then neutralized with dropwise addition of 29% NH$_3$/H$_2$O to pH 9.3 whereupon a precipitate may be formed. The precipitate may be removed by filtration, washed with distilled water (10 mL), and then dried under vacuum for 24 h, which may produce the product (estimated at 1.2 g).

Step C: To a round bottom flask may be added 3-furanylacrylic acid (0.95 g, 0.007 moles) followed by dichloromethane (10 mL) and 1 drop of dimethylformamide. Oxalyl chloride (1.07 g, 0.008 moles) may be added dropwise. This solution may be warmed to room temperature with stirring and held at that temperature for 2 h. Under reduced pressure, the solvent may be removed until a thick oil (crude 3-furanylacryloyl chloride) remains. Into a separate flask may be added 6α-N-methyl-(+)-naltrexamine (1.2 g, 0.003 moles) and dichloromethane (10 mL). After cooling the solution to ice bath temperature, triethylamine (1.02 g, 0.01 moles) may be added. Then, the previously prepared solution of crude 3-furanylacryloyl chloride in dichloromethane (5 mL) may be added dropwise. The ice bath may be removed and the reaction stirred for 2 h. Distilled water (10 mL) may be added and this mixture stirred for 1 h. The mixture may be transferred into a separatory funnel. The bottom organic layer may be separated and the volatile solvents in the organic layer may be evaporated under reduced pressure to produce a thick oil. To this oil may be added methanol (10 mL) followed by a 10% NaOH/H$_2$O solution (1.0 mL). This solution may be stirred for 1 hour at room temperature. The pH may be adjusted to 4.2 using glacial acetic acid. Distilled water (5 mL) containing NaHCO$_3$ (2 g) may be added. This mixture may be stirred for 1 hour at room temperature, followed by extraction with chloroform (3×25 mL). The extracts may be combined and dried over anhydrous MgSO$_4$ (1 g). The hydrated MgSO$_4$ may be removed by filtration. The solvents may be removed from the filtrate under reduced pressure affording an oil. The product (1.50 g) may be isolated by column chromatography with 2.5% MeOH/CHCl$_3$ elution.

Example 2

Preparation of (+)-Nalbuphine

The following reaction scheme depicts the synthesis of (+)-nalbuphine:

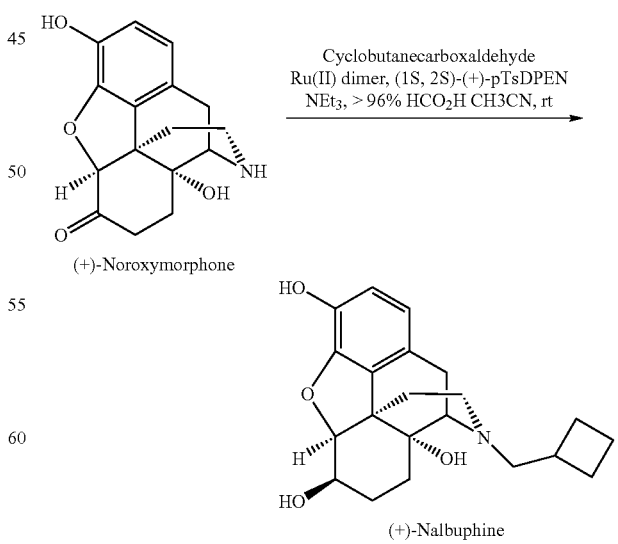

(+)-Noroxymorphone (1.5 g, 0.005 moles) may be dissolved in acetonitrile (10 mL). Cyclobutanecarboxaldehyde (0.88 g, 0.10 moles) may be then added and this reaction stirred at room temperature for 1 h. Then a mixture of triethylamine (2.64 g, 0.026 moles) and >96% formic acid (3.0 g, 0.065 moles) in acetonitrile (10 mL) may be added. Dichloro (p-cymene) Ru(II) dimer (16 mg) and (1S,2S)-(+)-para-toluenesulfonyl-1,2-diphenylethylenediamine (19 mg) may be then added. The reaction may be stirred at room temperature until the reaction is deemed complete by HPLC. Then, the reaction mixture may be evaporated to form a thick oil. Acetonitrile (10 mL) may be added and the reaction stirred at room temperature, wherein a precipitate may form. Filtration of this precipitate, and rinsing with acetonitrile (5 mL), may yield (+)-nalbuphine (estimate at 1.43 g).

What is claimed is:

1. A (+)-morphinan compound of Formula (II) or a pharmaceutically acceptable salt thereof:

(II)

wherein:
A is chosen from {—}$OR^8$ and {—}$NR^8R^9$;
$R^1$ is chosen from hydrocarbyl and substituted hydrocarbyl;
$R^3$, $R^4$, $R^8$, and $R^9$ are independently chosen from hydrogen, hydrocarbyl, and substituted hydrocarbyl;
$R^5$ and $R^6$ are independently chosen from hydrogen, hydrocarbyl, substituted hydrocarbyl, halogen, {—}OH, {—}$NH_2$, and {—}$OR^7$;
$R^7$ is chosen from hydrocarbyl and substituted hydrocarbyl;
Y is chosen from hydrogen, hydroxy, protected hydroxy, alkoxy, and acyloxy;
Z is chosen from hydroxy, protected hydroxy, alkoxy, and acyloxy; and
the dashed line between the carbon atoms at positions 7 and 8 represents a single bond or a double bond; provided, however:
when A is {—}OH, {—}O(CO)$CH_3$, {—}NH($CH_2$)$_2$OH, {—}NH(CO)$CH_3$, or {—}$NH_2$, then $R^1$ is other than methyl; when A is {—}OH, {—}NH($CH_2$)$_2$OH, or {—}NH(CO)$CH_3$, then $R^1$ is other than {—}($CH_2$(CH)$CH_2$; when A is {—}OH, {—}NH($CH_2$)$_2$OH, {—}NH(CO)$CH_3$, {—}$NH_2$, or {—}$NHCH_3$ then $R^1$ is other than {—}$CH_2$(cyclopropane); when A is {—}OH, then $R^1$ is other than {—}$CH_2$(cyclobutane); when A is —OC(═O)R, then R is H or heterocyclo; and, when A is —NR'R" and one of R' or R" is substituted alkyl, then the other of R' or R" is H.

2. The compound of claim 1, wherein $R^1$ is chosen from alkyl, cycloalkyl, cycloalkylmethyl, alkenyl, alkynyl, or aryl, and A is chosen from hydroxy, alkoxy, acyloxy, amine, alkyl substituted amine, amido, carbamyl, carbonate, and urea.

3. The compound of claim 1, wherein the compound has (+) optical activity, and wherein: the carbons at positions 5, 13, 14, and 9 have S, R, R, and S configurations, respectively, and the carbon at position 6 has an R or S configuration; or the substituted ring at position 5 is in the beta position and the Y at position 14 is in the alpha position.

4. The compound of claim 1, wherein the compound is of Formula (IIa) or a pharmaceutically acceptable salt thereof:

(IIa)

wherein:
A is chosen from {—}$OR^8$, and {—}$NR^8R^9$;
$R^1$ is chosen from hydrocarbyl and substituted hydrocarbyl;
$R^8$ and $R^9$ are independently chosen from hydrogen, hydrocarbyl, and substituted hydrocarbyl;
Y is chosen from hydrogen, hydroxy, protected hydroxy, alkoxy, and acyloxy; and
Z is chosen from hydroxy, protected hydroxy, alkoxy, and acyloxy; provided that when A is —NR'R" and one of R' or R" is substituted alkyl, then the other of R' or R" is H.

5. The compound of claim 4, wherein $R^1$ is chosen from alkyl, cycloalkyl, cycloalkylmethyl, alkenyl, alkynyl, or aryl; and A is chosen from hydroxy, alkoxy, acyloxy, amine, alkyl substituted amine, amido, carbamyl, carbonate, and urea.

6. The compound of claim 4, wherein the compound has (+) optical activity, and wherein: the carbons at positions 5, 13, 14, and 9 have S, R, R, and S configurations, respectively, and the carbon at position 6 has an R or S configuration; or the substituted ring at position 5 is in the beta position, and the Y at position 14 is in the alpha position.

7. The compound of claim 4, wherein the compound is chosen from (+)-nalbuphine and (+)-nalfurafine.

8. The compound of claim 1, wherein the compound is of Formula (IIb) or a pharmaceutically acceptable salt thereof:

(IIb)

wherein:
A is chosen from {—}$OR^8$ and {—}$NR^8R^9$;
$R^1$ is chosen from hydrocarbyl and substituted hydrocarbyl;
$R^8$ and $R^9$ are independently chosen from hydrogen, hydrocarbyl, and substituted hydrocarbyl;
Y is chosen from hydrogen, hydroxy, protected hydroxy, alkoxy, and acyloxy; and
Z is chosen from hydroxy, protected hydroxy, alkoxy, and acyloxy; provided that when A is —OC(═O)R, then R is H or heterocyclo.

9. The compound of claim 8, wherein $R^1$ is chosen from alkyl, cycloalkyl, cycloalkylmethyl, alkenyl, alkynyl, or aryl.

10. The compound of claim 8, wherein the compound has (+) optical activity, and wherein: the carbons at positions 5, 13, 14, and 9 have S, R, R, and S configurations, respectively, and the carbon at position 6 has an R or S configuration; or the substituted ring at position 5 is in the beta position, and the Y at position 14 is in the alpha position.

* * * * *